United States Patent [19]
Sirhan

[11] Patent Number: 5,195,971
[45] Date of Patent: Mar. 23, 1993

[54] PERFUSION TYPE DILATATION CATHETER

[75] Inventor: Motasim M. Sirhan, Santa Clara, Calif.

[73] Assignee: Advanced Cardiovascular Systems, Inc., Santa Clara, Calif.

[21] Appl. No.: 833,537

[22] Filed: Feb. 10, 1992

[51] Int. Cl.$^5$ ............................................. A61M 25/00
[52] U.S. Cl. ...................................... 604/96; 604/164
[58] Field of Search ................. 604/96, 102, 103, 164

[56] References Cited

U.S. PATENT DOCUMENTS

| | | |
|---|---|---|
| 4,597,755 | 7/1986 | Samson et al. ........................ 604/96 |
| 4,661,094 | 4/1987 | Simpson . |
| 4,744,366 | 5/1988 | Jang . |
| 4,762,129 | 8/1988 | Bonzel .................................. 604/96 |
| 4,763,654 | 8/1988 | Jang . |
| 4,771,777 | 9/1988 | Horzewski et al. . |
| 4,782,834 | 11/1988 | Maguire et al. ....................... 604/96 |
| 4,790,315 | 12/1988 | Mueller, Jr. et al. . |
| 4,877,031 | 10/1989 | Conway et al. ....................... 604/96 |
| 4,892,519 | 1/1990 | Songer et al. ......................... 604/96 |
| 4,909,252 | 3/1990 | Goldberger . |
| 4,917,667 | 4/1990 | Jackson ................................. 604/96 |
| 4,944,745 | 7/1990 | Sogard et al. ......................... 604/96 |
| 4,955,895 | 9/1990 | Sugiyama et al. .................... 604/96 |
| 4,977,894 | 12/1990 | Davies ................................... 604/96 |
| 4,983,167 | 1/1991 | Sahota . |
| 4,988,356 | 1/1991 | Crittenden et al. .................. 604/96 |
| 4,990,139 | 2/1991 | Jang . |
| 4,998,917 | 3/1991 | Gaiser et al. ......................... 604/96 |
| 5,035,694 | 7/1991 | Kasprzyk et al. .................... 604/96 |

Primary Examiner—Paul J. Hirsch
Attorney, Agent, or Firm—Crosby, Heafey, Roach & May

[57] ABSTRACT

A dilatation catheter is described wherein a primary perfusion port is provided adjacent the proximal end of the inflatable member having a transverse cross-sectional area which is dimensioned to provide the bulk of the perfusion flow through the catheter. The primary perfusion port is offset from the guidewire receiving lumen which extends through the catheter shaft.

14 Claims, 3 Drawing Sheets

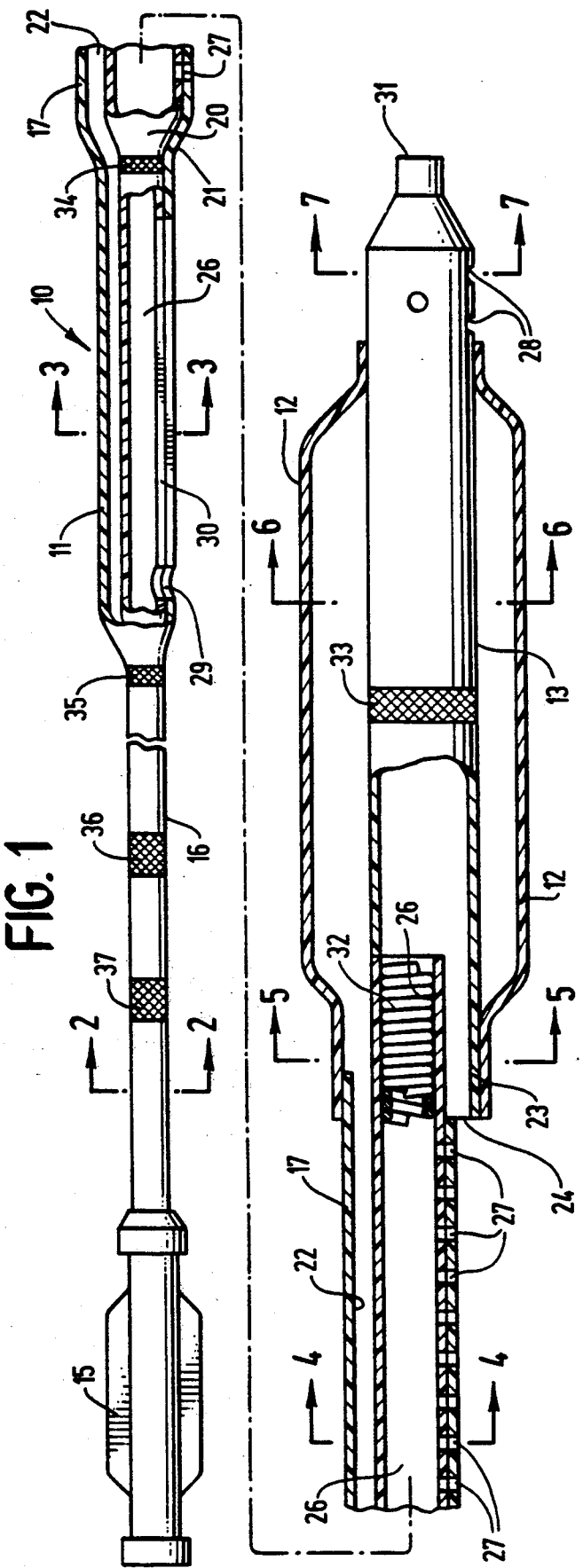

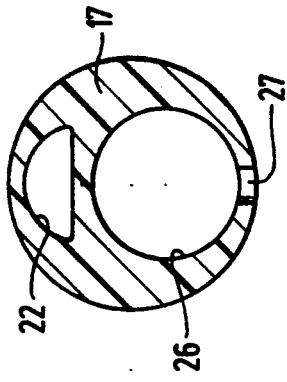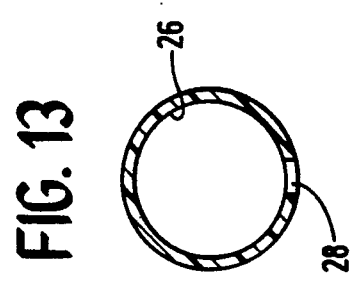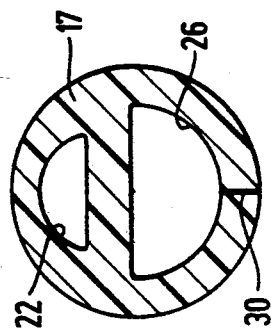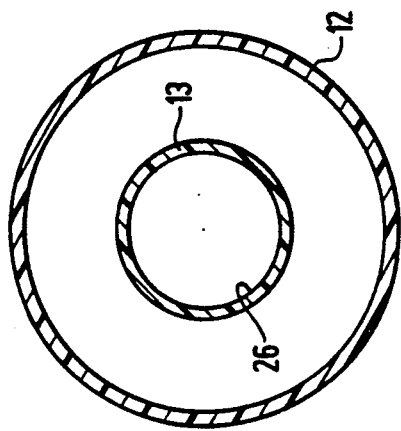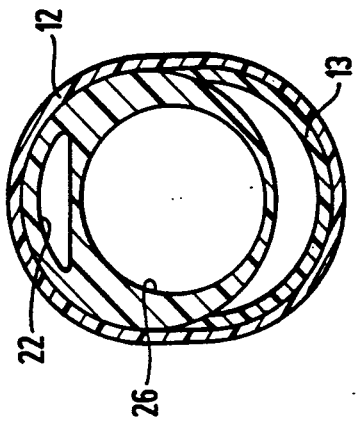

PERFUSION TYPE DILATATION CATHETER

BACKGROUND OF THE INVENTION

This invention generally relates to perfusion type dilatation catheters, such as balloon dilatation catheters used in percutaneous transluminal coronary angioplasty (PTCA).

In classic PTCA procedures, a guiding catheter having a preshaped distal tip is percutaneously introduced into the cardiovascular system of a patient and advanced therein until the preshaped distal tip of the guiding catheter is disposed within the aorta adjacent the ostium of the desired coronary artery. The guiding catheter is twisted or torqued from the proximal end to turn the distal tip of the guiding catheter so that it can be guided into the desired coronary ostium. With over-the-wire systems, a guidewire and a balloon dilatation catheter are introduced into and advanced through the guiding catheter to the distal tip thereof, with the guidewire slidably disposed within an inner lumen of the dilatation catheter. The guidewire is first advanced out the distal tip of the guiding catheter, which is seated in the ostium of the patient's coronary artery, until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4–12 atmospheres) to dilate the stenosed region of the diseased artery. One or more inflations may be necessary to effectively dilate the stenosis. Additional stenoses may be dilatated with the same catheter. When the dilatations are completed, the balloon is deflated to that the dilatation catheter can be removed from the dilated stenosis and blood flow will resume through the dilated artery.

Further details of guiding catheters, dilatation catheters, guidewires, and other devices for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); and U.S. Pat. No. 4,898,577 (Badger et al.) which are hereby incorporated herein in their entirety by reference thereto.

The assignee of the present application, Advanced Cardiovascular Systems, Inc. introduced an improved dilatation catheter into the market place under the trademark STACK PERFUSION ® Coronary Dilatation Catheter which has a plurality of perfusion ports in the wall of the catheter shaft proximal to the balloon and has one or more perfusion ports in the catheter shaft distal to the balloon. The perfusion ports are in fluid communication with an inner lumen which extends to the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the inflated balloon to thereby prevent or minimize ischemic conditions in tissue distal to the catheter when the balloon is inflated. As is appreciated by those skilled in the art, tissue distal to a stenosis is frequently already in jeopardy due to ischemic conditions which may exist due to the stenotic region within the artery. As a result, care must be exercised in sizing the perfusion ports and the inner lumen to ensure that there is adequate flow of oxygenated blood to tissue distal to the catheter to eliminate or minimize ischemic conditions. This perfusion catheter has been widely praised and has met with much commercial success.

The assignee of the present invention also markets an improved dilatation catheter under the registered trademark ASC RX ® Coronary Dilatation Catheter which is described and claimed in U.S. Pat. No. 5,040,548 (Yock), U.S. Pat. No. 5,061,273 (Yock) and U.S. Pat. No. 4,748,982 (Horzewski et al.) and which has a short guidewire receiving sleeve or inner lumen extending through a distal portion of the catheter. The sleeve or inner lumen extends proximally a distance of at least about 10 cm from a first guidewire port in the distal end of the catheter to a second guidewire port in the catheter spaced proximally from the inflatable member of the catheter. The second guidewire port is spaced a substantial distance from the proximal end of the catheter and usually not more than about 50 cm from the first guidewire port in the distal end of the catheter. Preferably, a slit is provided in the wall of the catheter body which extends distally from the second guidewire port, preferably to a location proximal to the proximal end of the inflatable balloon. The structure of this catheter allows for the rapid exchange of the catheter without the need for an exchange wire or adding a guidewire extension to the proximal end of the guidewire. The design of this catheter has likewise been widely praised by the medical profession and has been met with much success in the market place because of the advantages of its unique design.

One of the major deficiencies of a perfusion type dilatation catheter has been that the inner lumen, which is adapted to receive the guidewire and to perfuse blood through the interior of the balloon, has such a large diameter that the use of the catheter has been limited to the more proximal stenoses. The present invention minimizes the diameter of the inner perfusion lumen and therefore satisfies this need.

SUMMARY OF THE INVENTION

This invention is directed to a perfusion type dilatation catheter and particularly to a perfusion type catheter which is readily exchangeable without the need for guidewire extension wires or exchange wires.

The catheter of the invention generally includes an elongated catheter shaft with proximal and distal sections and an inner lumen which extends within the catheter shaft to the distal end thereof. A tubular element, which has proximal and distal ends, is secured by its proximal end to the distal end of the catheter shaft and has an inner lumen extending within the tubular element to guidewire port in the distal end thereof which is in fluid communication therewith. A portion of the proximal end of the tubular element extends proximally beyond the distal end of the catheter and defines a perfusion port which is offset from the inner lumen within the catheter shaft. The dimensions of the perfusion port defined by the proximal end of the tubular element are selected so that at least 25%, preferably at least 50% of the perfusion flow through the catheter passes through this perfusion port. One or more additional perfusion ports may be provided in the catheter shaft proximal to the first mentioned perfusion port which are in fluid communication with the inner lumen therein to assist in the delivery of blood distal to the catheter. An inflatable member, such as a balloon, is disposed about the tubular element with the distal end of the inflatable member sealingly secured about the distal end of the tubular element. The proximal end of the inflatable member is sealingly secured about the distal end of the catheter shaft and the portion of the proximal end of the tubular element.

In one presently preferred embodiment, the distal portion of the catheter shaft proximal to the perfusion port is provided with a guidewire receiving port which is in fluid communication with the inner lumen within the catheter shaft, such as described in U.S. Pat. No. 5,040,548 (Yock), U.S. Pat. No. 5,061,273 (Yock), and U.S. Pat. No. 4,748,982 (Horzewski et al.), which are incorporated herein. The guidewire port in the proximal section is spaced longitudinally from the guidewire port in the distal end of the tubular element a distance of at least about 10 cm but generally not greater than about 50 cm. In this embodiment, it is preferred that the proximal portion of the catheter shaft have a greater degree of stiffness to aid in pushing the catheter over a guidewire. The proximal shaft portion is preferably formed, at least in part, of hypotubing.

The catheter of the invention provides for a greatly increased perfusion flow of blood through the catheter and allows the guidewire to be withdrawn into the proximal part of the distal section of the catheter shaft without fear of withdrawing the guidewire completely from the catheter. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 9 is a transverse cross-sectional view of the catheter shown in FIG. 8 taken along the line 9—9.

FIG. 10 is a transverse cross-sectional view of the catheter shown in FIG. 8 taken along the lines 10—10.

FIG. 11 is a transverse cross-sectional view of the catheter shown in FIG. 8 taken along the lines 11—11.

FIG. 12 is a transverse cross-sectional view of the catheter shown in FIG. 8 taken along the lines 12—12.

FIG. 13 is a transverse cross-sectional view of the catheter shown in FIG. 8 taken along the lines 13—13.

DETAILED DESCRIPTION OF THE INVENTION

Figure 7:
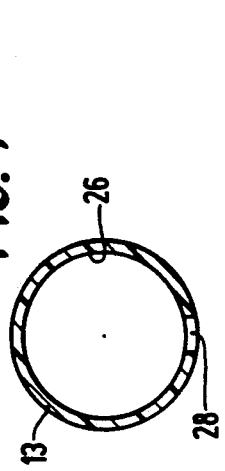
FIG. 7 is a transverse cross-sectional view of the catheter shown in FIG. 1 taken along the lines 7—7.
Figure 6:
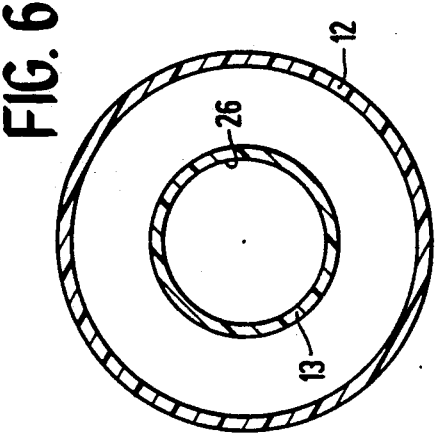
FIG. 6 is a transverse cross-sectional view of the catheter shown in FIG. 1 taken along the lines 6—6.

A catheter 10, embodying features of the invention, is depicted in FIGS. 1-7 and generally includes a catheter shaft 11, a tubular extension 13, a balloon 12 disposed about the tubular extension, and an adapter 15 which is secured to the proximal end of the catheter shaft.

Figure 5:
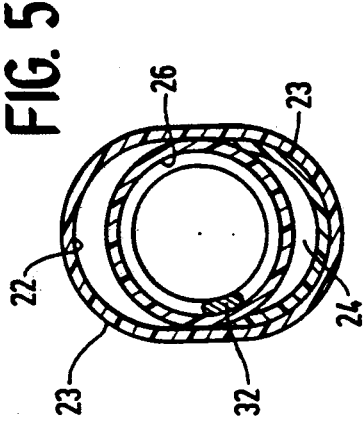
FIG. 5 is a transverse cross-sectional view of the catheter shown in FIG. 1 taken along the lines 5—5.
Figure 8:
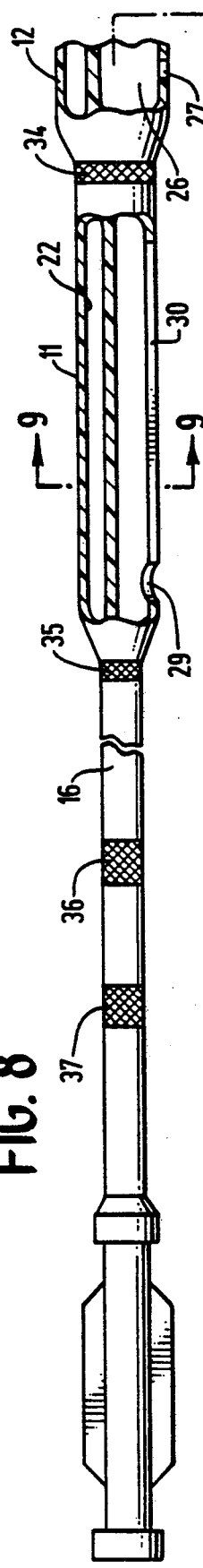
FIG. 8 is a elevational view, partially in section, of an alternative embodiment of the invention.

The catheter shaft 11 includes a proximal section 16 and a distal section 17. The proximal section is formed of hypotubing 18 and an outer coating or jacket 19 as shown in FIG. 2 and is generally stiffer than the distal section 17. The distal section 17 is of a fused coaxial design which is disclosed in co-pending application Ser. No. 07/700,617, filed on May 15, 1991, entitled LOW PROFILE DILATATION CATHETER, which is incorporated herein by reference. The fused distal section 17 has an inner tubular memebr 20 and an outer tubular member 21 having a significant portion thereof which is secured to the inner tubular member, as shown. Preferably, the outer tubular member 21 is formed of a heat shrinkable plastic material which is heat shrunk onto the inner tubular member 20, and which has a mandrel between the inner and outer tubular members so that, upon the heat shrinking of the outer tubular member 21, the inflation lumen 22 is formed. The outer tubular member 21 may also be heat bonded or adhesively bonded to the inner tubular member 20. The proximal portion 23 of the tubular extension 13 is secured to the distal end of the distal section 17 of the catheter shaft 11. As shown in FIGS. 1 and 5, the lower proximal portion 23 of the tubular extension 13, which extends proximally beyond the distal end of the distal section 17, defines a primary proximal perfusion port 24 which is offset from the inner lumen 26 extending within the catheter shaft 11 and which is dimensioned to handle the bulk of the perfusion flow through the catheter 10. The distal part of the distal section 17 is provided with a plurality of secondary proximal perfusion ports 27 which extend through the bonded sections of the inner tubular member 20 and outer tubular member 21 as best shown in FIGS. 1 and 4. One or more distal perfusion ports 28 is provided in the tubular extension 13 for the discharge of blood into the artery distal to the catheter 10. The proximal part of the distal section 17 is provided with a proximal guidewire port 29 which is in fluid communication with the inner lumen 26 and with a slit 30 is the catheter shaft wall which is also in fluid communication with the inner lumen 26 and which extends distally from the proximal guidewire port 29. The inner lumen 26 extends through the tubular extension 13 to a distal guidewire port 31 in the distal end of the catheter 10. Substantial amounts of blood may perfuse through the distal guidewire port 31 when a guidewire is not extending therethrough. A coil 32 may be provided within the distal end of the inner tubular member 20 for purposes of support when the balloon 14 is inflated and to also provide a smoother transition between distal section 17 of the catheter shaft 11 and the tubular extension 13. While the balloon 12 and the outer tubular member 21 are shown as separate but joined together, they may be formed together in a unitary structure.

The distal end of the hypotube 18 is usually tapered and interfit into the proximal end of the outer tubular member 21. The structure of this portion of the catheter including the proximal end of the inner member 21 is illustrated in the above described copending application Ser. No. 07/700,617, which has been incorporated herein.

Radiopaque marker 33 is provided on the tubular extension 13 at the midpoint of the balloon 12, on the catheter shaft 11 proximal to the secondary perfusion holes 27, and on the catheter shaft proximal to the proximal guidewire port 29, respectively, to facilitate fluoroscopic observation of the distal section of the catheter shaft within the patient. Visual markers 36 and 37 are provided on the proximal section of the catheter shaft, with marker 37 being the femoral marker located about 105 cm from the distal end of the catheter and marker 36 being the brachial marker located about 95 cm from the distal end of the catheter.

FIGS. 8-13 illustrate an alternative embodiment of the invention wherein the distal section 17 of the catheter shaft 11 is formed of a dual lumen extruded section 37 with a crescent or D-shaped inflation lumen 22 extending the entire length of the distal section and the guidewire lumen 26 being crescent or D-shaped in the proximal part of the distal section 17 and circular in the distal part thereof as depicted in FIGS. 9 and 10. The rest of the catheter is essentially the same as that shown in FIGS. 1-7 and the components thereof are numbered the same.

The materials of construction can be of a conventional nature. The hypotube 18 can be formed of stainless steel or a superelastic NiTi alloy, such as described and claimed in copending application Ser. No. 07/629,381, filed Dec. 18, 1990, and incorporated herein by reference, and the coating or jacket 19 thereon can be a polyethylene tubing heat shrunk onto the exterior of the hypotube. The inner and outer tubular members 20 and 21 of the embodiment shown in FIG. 1, the extruded section 37 of the embodiment shown in FIG. 8, and the tubular section 13, shown in both embodiments, may be formed of mixture of high and low density heat shrinkable polyethylene. Generally the inner member is predominately high density polyethylene and the outer tubular member is predominantly low density polyethylene. The balloon 12 may be formed of polyethylene, polyethylene terephthalate, ionomers such as Suryln ® (sold by E.I. duPont, deNemours & Co.) and other suitable materials. The balloon can be a formed-in-place balloon which is described in copending application Ser. No. 07/758,630, filed Sep. 12, 1991, entitled FORMED IN PLACE BALLOON FOR VASCULAR CATHETER and which is incorporated herein by reference. The joints between the various members of the catheter can be made by heat bonding or by means of a suitable adhesive such a cyanoacrylate adhesive sold under the trademark Loctite TM, e.g. 405 and 415.

The dimensions of the catheter are for the most part conventional. The overall length of the catheter, excluding the adapter is about 135 cm, the length of the distal section is about 28 cm, the cylindrical working surface of the balloon is about 2 cm. The maximum inflated diameters of the balloon generally range from about 1 to about 4 mm. The transverse dimensions of the catheter shaft are controlled by the outer diameter of the guidewire to be used in the angioplasty procedure. The guidewires conventionally used have outer diameters ranging from about 0.010 to about 0.018 inch (0.25 to 0.46 mm). The inner diameters of the guidewire receiving inner lumens for guidewires of this size generally range from about 0.012 to about 0.022 inch (0.38 to 0.56 mm). Typical wall thicknesses for the inner and outer tubular members is about 0.002 inch (0.051 mm). The wall thickness of the balloon varies depending upon the material from which it is made and the level of pressure the balloon is to experience upon inflation during the angioplasty procedure. The cross-sectional area of the primary perfusion port can vary depending upon the size of the catheter, the size of the artery into which the catheter is to be deployed and whether secondary perfusion ports are to be provided.

The invention has been described herein primarily with respect to dilatation catheters having rapid exchange features, namely, a short guidewire receiving inner lumen within the distal section of the catheter with a proximal guidewire port spaced at least 10 cm proximately from a distal guidewire port in the distal end of the catheter. However, the features of the invention can be employed in a wide variety of perfusion type catheters used in various body lumens.

What is claimed is:

1. A perfusion type catheter comprising:
   a) an elongated catheter shaft having proximal and distal sections and an inner tubular member with a distal end and a guidewire receiving lumen extending within the inner tubular member to the distal end thereof;
   b) an inflatable dilatation member on the distal section of the catheter shaft; and
   c) a tubular extension, having proximal and distal sections, extending through the interior of the inflatable dilatation member, being connected to a distal portion of the inner tubular member having an inner lumen in fluid communication with the guidewire receiving lumen within the tubular member with an interior proximal section of the tubular extension defining a primary perfusion port which is offset from and proximal to the distal end of the tubular member having the guidewire receiving lumen.

2. The catheter of claim 1 wherein the catheter shaft has an outer tubular member which defines with the inner tubular member an inflation lumen extending therein which is fluid communication with the interior of the inflatable member and wherein the catheter shaft has means provided on the proximal end thereof to inject inflation liquid through the inflation lumen to the interior of the inflatable member.

3. The catheter of claim 1 wherein the distal section of the catheter shaft has a plurality of secondary perfusion ports in fluid communication with the guidewire receiving lumen extending through the tubular member.

4. The catheter of claim 1 wherein the catheter shaft tubular extension has a guidewire port in the distal portion thereof in fluid communication with the guidewire receiving lumen within the inner tubular member and spaced at least 10 cm from the distal end of the tubular extension, proximal to the primary perfusion port and a substantial distance from the proximal end of the catheter shaft.

5. The catheter of claim 1 wherein the primary perfusion port is dimensioned to provide at least about 25% of the perfusion flow through the catheter.

6. The catheter of claim 1 wherein the primary perfusion port is dimensioned to provide at least about 50% of the perfusion flow through the catheter.

7. The catheter of claim 2 wherein in the distal section of the catheter shaft the outer tubular member is secured to the exterior of the inner tubular member for a significant portion thereof and has an unsecured portion which defines the inflation lumen.

8. The catheter of claim 7 wherein the catheter shaft is provided with a proximal guidewire port which is located at least 10 cm from the distal end of the tubular extension and proximal to the primary perfusion port and which is in fluid communication with the inner lumen extending within the tubular member.

9. The catheter of claim 8 wherein the catheter shaft is provided with secondary perfusion ports which are located proximal to the primary perfusion port and distal to the proximal guidewire port and which are in fluid communication with the guidewire lumen within the tubular member.

10. The catheter of claim 1 wherein perfusion ports are provided in a distal section of the tubular extension.

11. The catheter of claim 1 wherein a helical coil is disposed within the guidewire receiving lumen in the distal end of the tubular member.

12. The catheter of claim 7 wherein the secured portion of catheter shaft is provided with a slit which extends distally from the proximal guidewire port to facilitate the removal of the catheter from a guidewire.

13. The catheter of claim 1 wherein the distal section of the catheter shaft has a D-shaped inflation lumen extending therein to the interior of the inflatable member.

14. The catheter of claim 13 wherein the distal section of the catheter shaft has a D-shaped guidewire receiving inner lumen extending distally from a proximal guidewire port.

* * * * *